(12) United States Patent
Linington et al.

(10) Patent No.: US 9,321,811 B2
(45) Date of Patent: Apr. 26, 2016

(54) FURTHER NOVEL ANTI-PARASITIC COMPOUNDS

(71) Applicants: Roger Linington, Santa Cruz, CA (US); Laura Sanchez, Santa Cruz, CA (US)

(72) Inventors: Roger Linington, Santa Cruz, CA (US); Laura Sanchez, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/256,154

(22) Filed: Apr. 18, 2014

(65) Prior Publication Data

US 2014/0221276 A1    Aug. 7, 2014

Related U.S. Application Data

(63) Continuation of application No. 13/256,498, filed as application No. PCT/US2010/028071 on Mar. 20, 2010, now Pat. No. 8,772,247.

(60) Provisional application No. 61/210,657, filed on Mar. 20, 2009.

(51) Int. Cl.
*C07K 7/06* (2006.01)
*A61K 38/00* (2006.01)

(52) U.S. Cl.
CPC .. *C07K 7/06* (2013.01); *A61K 38/00* (2013.01)

(58) Field of Classification Search
None
See application file for complete search history.

(56) References Cited

U.S. PATENT DOCUMENTS 9,115,133 B2    8/2015    Baraekar et al.

OTHER PUBLICATIONS

Alberts et al (Molecular Biology of the Cell. 4th edition, New York: Garland Science; 2002; retrieved from http://www.ncbi.nlm.nih.gov/books/NBK26917/ on Mar. 2, 2015, 10 pages).*
Davies J ('Millenium bugs' TCB v9(12) 1999 pp. M2-M5).*

* cited by examiner

*Primary Examiner* — Karlheinz R Skowronek
*Assistant Examiner* — Ronald Niebauer
(74) *Attorney, Agent, or Firm* — Adam Warwick Bell; Matthew Rupert Kaser

(57) ABSTRACT

A novel structural class of highly N-methylated linear lipopeptide compounds useful for the treatment of parasitic disease.

4 Claims, 5 Drawing Sheets

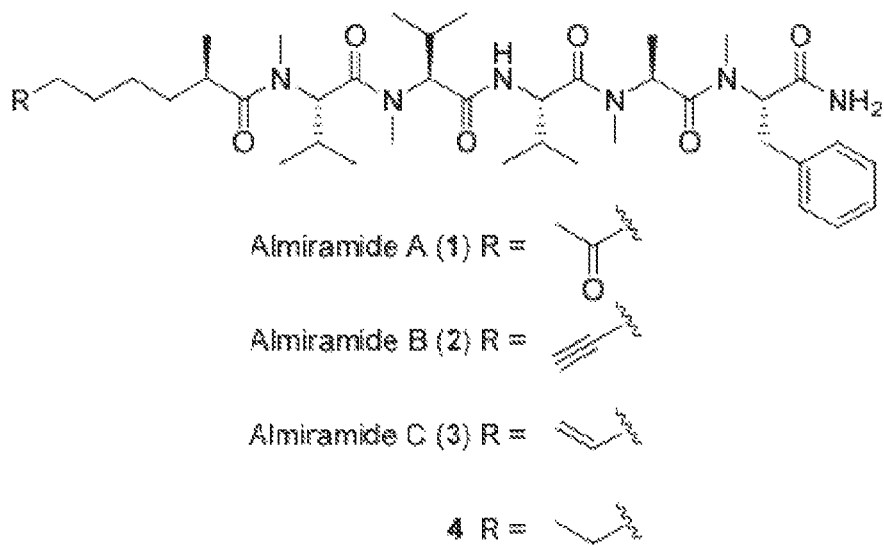
FIG. 1a: Almiramides A, B and C
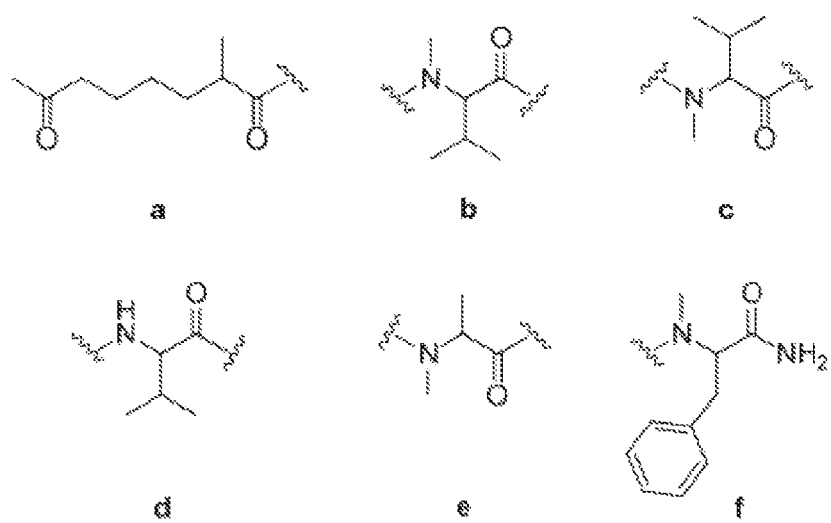
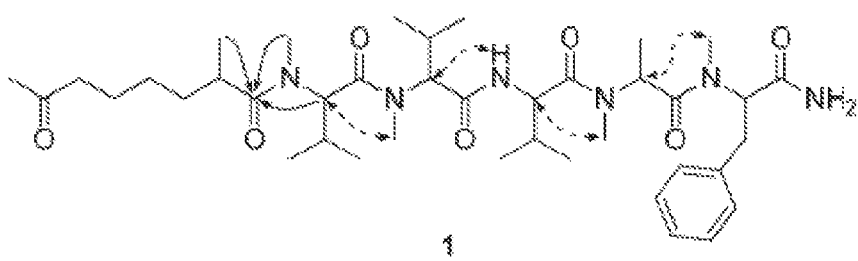
FIG. 1b. Subunits a - f and NMR connectivity for 1. Solid arrows = HMBC correlations. Dashed arrows = ROESY correlations.

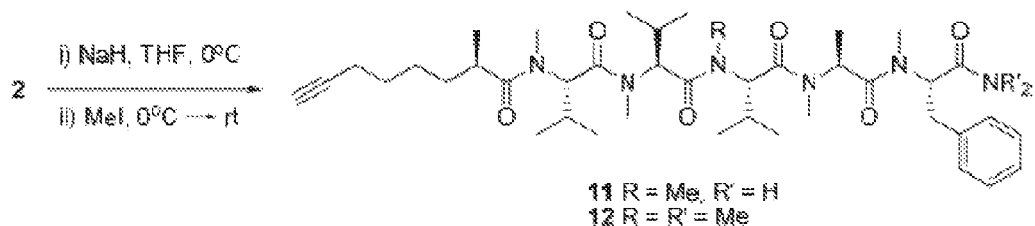
FIG. 2: Selective semisynthetic methylation of 2 to afford compounds 11 and 12
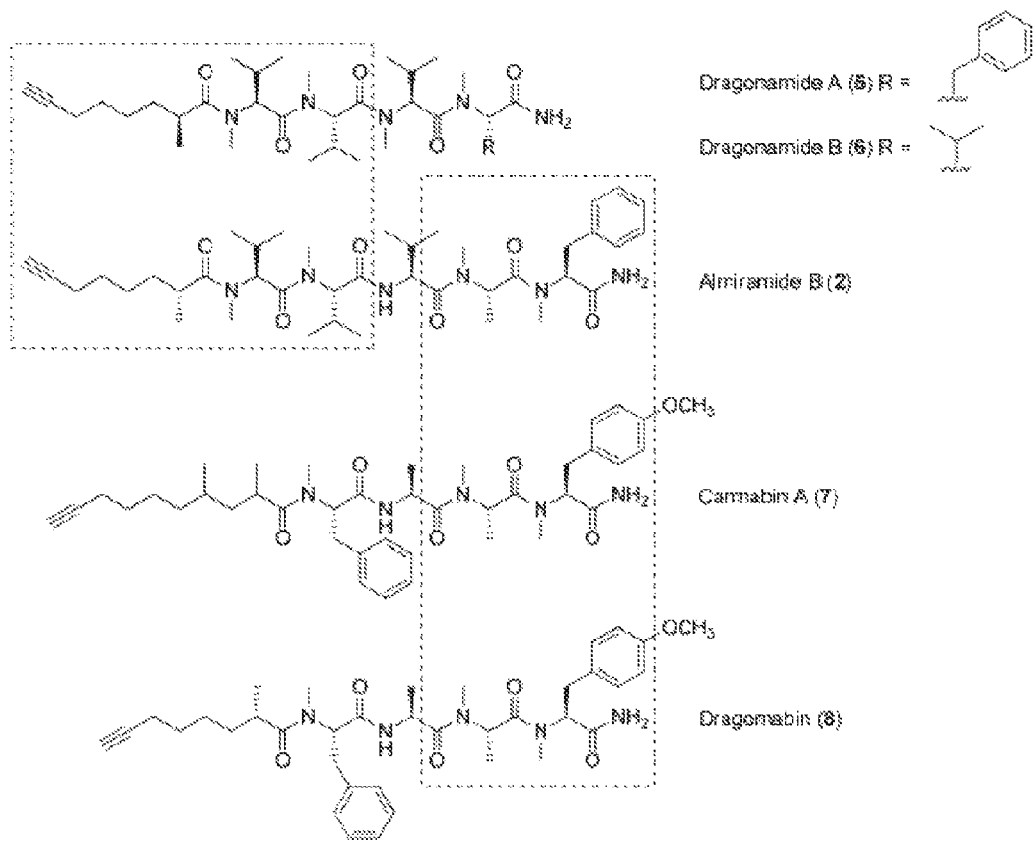
Figure 3. Structurally related linear lipopeptides (areas of highest structural homology outlined with dashed lines).
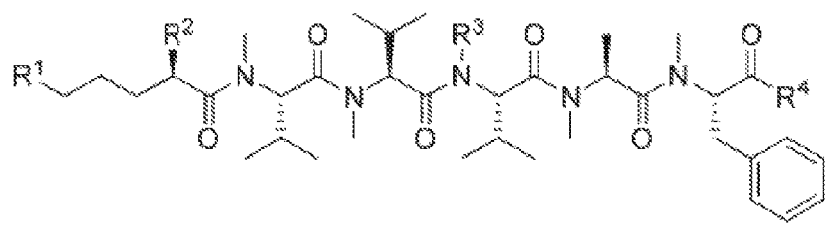
FIG. 4. Generic structure of Almiramide.

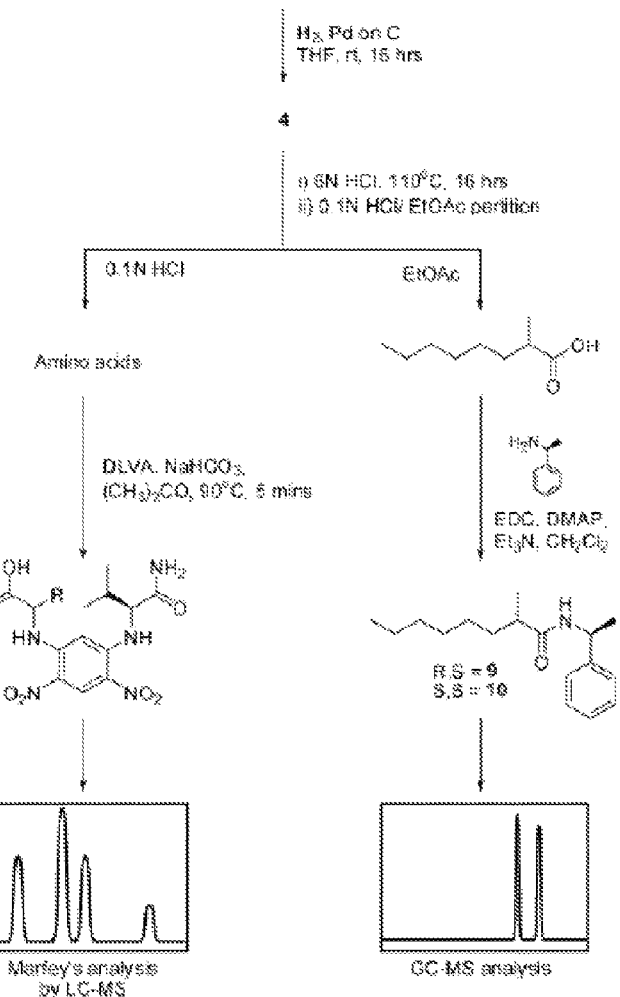
FIG. 5  Configurational analysis strategy for 2 and 3.
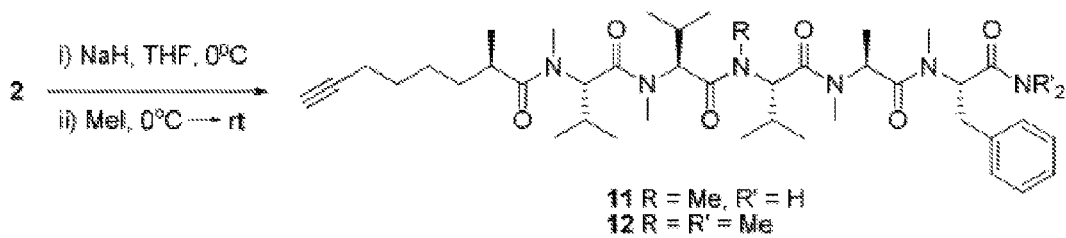
FIG. 6  Formation of semi-synthetic derivatives 11 and 12.

FIG.7 Structure and Bioactivities of Almiramide A – C and Derivatives.
1 - 3 are natural products, 4, 11 and 12 are semi-synthetic analogues from natural products, and 13 - 24 are entirely new synthetic compounds created by the applicant.

| Compound | $R^1$ | $R^2$ | $R^3$ | $R^4$ | Bioactivity (μM) | | |
|---|---|---|---|---|---|---|---|
| | | | | | *Leishmania donovani* | Macrophage assay | Cytotoxicity (Vero cells) |
| 1 | | Me | H | $NH_2$ | >13.5 | 13.4 | 113.1 |
| 2 | | Me | H | $NH_2$ | 2.4 | 11.0 | 52.3 |
| 3 | | Me | H | $NH_2$ | 1.9 | 4.3 | 33.1 |
| 4 | | Me | H | $NH_2$ | >13.7 | nt | nt |
| 11 | | Me | Me | $NH_2$ | 1.6 | nt | nt |
| 12 | | Me | Me | $NMe_2$ | 2.3 | nt | nt |
| 13 | | H | Me | $NMe_2$ | 5.9 | nt | 159.4 |
| 14 | | H | Me | $NMe_2$ | 2.7 | nt | 23.8 |
| 15 | | H | Me | $NMe_2$ | 3.1 | nt | 155.7 |
| 16 | | H | Me | $NMe_2$ | 6.7 | nt | 93.1 |
| 17 | | H | Me | OH | >14.0 | nt | nt |
| 18 | | H | Me | OH | 4.1 | Nt | 192.4 |

(FIG. 7 continued)
| 19 |  | H | Me | OH | 5.6 | Nt | 231.1 |
| 20 | 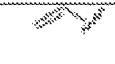 | H | Me | OH | >14.0 | Nt | nt |
| 21 |  | H | Me | OMe | >14.0 | Nt | nt |
| 22 |  | H | Me | OMe | >14.0 | Nt | nt |
| 23 |  | H | Me | OMe | >14.0 | Nt | nt |
| 24 |  | H | Me | OMe | >14.0 | Nt | nt |

FURTHER NOVEL ANTI-PARASITIC COMPOUNDS

RELATIONSHIP TO OTHER APPLICATIONS

This application claims the benefit of and priority to U.S. application Ser. No. 13/256,498 filed 10 Nov. 2011 (371(c) date), which is a U.S. National Phase Application of PCT/US 10/28071 filed 20 Mar. 2010, which itself claims the benefit of and priority to U.S. provisional application No. 61/210,657 filed 20 Mar. 2009, all of which applications are hereby incorporated by reference for all purposes.

GOVERNMENT SPONSORSHIP

None
This invention was made with Government support under Grant No. TW006634, awarded by the National Institutes of Health. The Government has certain rights in this invention

FIELD OF THE INVENTION

The invention relates to a new structural class of compounds for the treatment of diseases, particularly parasitic diseases such as, but not limited to, leishmaniasis and sleeping sickness. The invention relates to these new compounds and their derivatives and analogues that have been shown to demonstrate clinically relevant levels of therapeutic activity. The invention further relates to the synthesis and use of such compounds in the treatment of disease, and to the production of drug formulations containing such compounds.

BACKGROUND

Leishmaniasis is a debilitating disease prevalent across many inter-tropical regions of the world including India, Sudan and Brazil. Caused by over twenty species of intracellular parasite from the genus *Leishmania*, leishmaniasis can present itself in a number of different clinical manifestations including cutaneous, mucosal and visceral forms of the disease. Both the cutaneous and mucosal forms can cause severe disfigurement to patients including ulcerative skin lesions and the destruction of the mucous membranes of the nose, mouth and throat leading to permanent disfigurement and frequent social ostracization. However it is the visceral form of the disease that represents the greatest threat to human health, with symptoms ranging from fever and weight loss in the initial stages to the development of spleneomegaly (a dramatic enlargement of the spleen) and ultimately multisystem infection and death in untreated cases. Visceral leishmaniasis is caused by a small sub-group of the *Leishmania* parasites, principally *L. donovani*, *L. infantum* and *L. chagasi*. Current treatment is limited to only a few viable alternatives, each of which suffers from drawbacks either in terms of efficacy, toxicity or cost. Until recently the most widely used therapeutic in most regions of the world was pentavalent antimony. Though initially highly efficacious with an estimated 90-95% cure rate in most areas after its introduction in the 1950's, this treatment has suffered from increasing emergence of resistance fuelled by the high rate of patient non-compliance due to the exceedingly long treatment period. Additionally the relatively high toxicity of this treatment regimen kills an estimated 2-5% of patients as a direct effect of drug toxicity. Alternative therapeutics include liposomal amphotericin B which is highly effective and requires only a short course of treatment but is too expensive to be a viable treatment option in most developing nations, and miltefosine, an alkylphospholipid recently licensed for use against visceral leishmaniasis in India, Germany and Colombia which has shown excellent cure rates, but which is also already facing instances of resistance in some areas. This shortfall of affordable and clinically efficacious treatments has led the World Health Organization to designate leishmaniasis as a category 1 disease, signifying that it is an emerging and uncontrolled global health problem. There is clearly therefore a pressing need for the development of new drugs to treat leishmaniasis, and it is with this aim that the Panama International Cooperative for Biodiversity Group (ICBG) is investigating Panamanian microorganisms for lead compounds with antileishmanial activity.

Human African trypanosomiasis or Sleeping sickness is a parasitic disease of people and animals, caused by protozoa of the species *Trypanosoma brucei* and transmitted by the tsetse fly. The disease is endemic in some regions of Sub-Saharan Africa, covering about 36 countries and 60 million people. It is estimated that 50,000 to 70,000 people are currently infected. The current standard treatment for first stage trypanosomiasis employs administering intravenous pentamidine (for *T.b. gambiense*) or intravenous suramin (for *T.b. rhodesiense*). Alternative first line therapies include using intravenous melarsoprol with or without oral nifurtimox. Intravenous eflornithine may also be used. The current standard treatment for second stage (later stage) disease uses intravenous melarsoprol.

BRIEF DESCRIPTION OF THE INVENTION

The inventors have discovered a new class of compounds (highly N-methylated linear lipopeptides) that possess novel structures that are believed to be entirely novel and to have no precedent in the literature.

The inventors have proven that these compounds possess clinically significant anti-parasitic activity, particularly against protozoan parasites including *Leishmania donovani* and *Trypanosoma brucei*. The anti-parasitic activity experimentally demonstrated against both *Leishmania donovani* and *Trypanosoma brucei* is better than those of currently available therapeutic compounds, without showing significant cytotoxicity to mammalian Vero cells.

Through the research of the inventors it is clear that this new structural class of compounds may be used for the treatment of diseases, particularly parasitic diseases such as, but not limited to, leishmaniasis and sleeping sickness.

The invention relates to these new compounds (and/or to their derivatives and analogues, sub-components and fragments derived therefrom) that demonstrate clinically relevant levels of therapeutic activity.

The invention further relates to the synthesis and use of such compounds in the treatment of disease, and to the production of drug formulations containing such compounds.

The invention further encompasses drug targets that bind specifically to the compounds of the invention (and/or to their derivatives and analogues, sub-components and fragments derived therefrom), and methods for identifying drug targets by contacting a sample containing one or more putative targets with one or more compounds of the invention and/or to their derivatives and analogues, sub-components and fragments derived therefrom. A sample may contain material derived, for example, from a pathogenic organism, such as a parasite, such as a eukaryotic pathogen, such a pathogenic amoeba or protozoa.

In particular, the applicant has discovered that various linear lipopeptide compounds derived from the marine cyanobacterium *Lyngbya majuscula* possess anti-parasitic properties, particularly against the organisms that cause leishmaniasis and sleeping sickness. The applicant has performed isolation, analysis, biological evaluation and synthesis of the highly N-methylated linear lipopeptides: Almiramides A-C, disclosed herein.

Bioassay guided fractionation has led to the discovery of a new structural class of compounds for the treatment of parasitic diseases, for example, leishmaniasis with clinically relevant levels of activity. The new compounds are highly N-methylated linear lipopeptides: Almiramides. The organic extract of a Panamanian collection of the marine cyanobacterium *Lyngbya majuscula* showed strong in vitro activity in two complementary screens against the tropical parasite *Leishmania donovani*, one of the causative agents of leishmaniasis. Chromatographic separation of this complex mixture led to the isolation of the highly N-methylated linear lipopeptides—Almiramides A-C (1-3) as the active constituents of this extract, as well as the known metabolite dragonamide B (6). Comparison with the biological activities of a number of related metabolites and semi-synthetic derivatives revealed key features required for activity and afforded one new compound (11) with superior in vitro activity against *L. donovani*. Derivatization of the hydrolysis products for almiramide B (2) followed by GC-MS analysis showed the 2-methyloct-7-ynoic acid terminus to possess the R configuration in contrast to other metabolites from this extract which contained the closely related (s)-2-methyloct-7-ynoic acid terminus, providing evidence for an unusual degree of biosynthetic specificity in the production of closely related compounds from this organism. Finally, synthesis of a library of simplified synthetic analogues afforded several compounds with superior potency to the natural products which paves the way for further drug development.

Certain specific embodiments appear in the claims, and additionally include the following: An almiramide molecule, or a derivative thereof, comprising a linear lipopeptide having the following structure

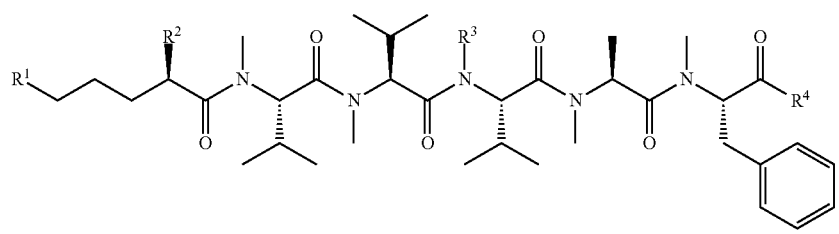

but specifically excluding compounds (1), (2) and (3) wherein for (1), $R^1$ consists of

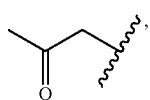

$R^2$ consists of Me, $R^3$ consists of H, and $R^4$ consists of NH2; and wherein for (2), $R^1$ consists of

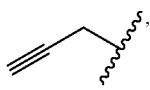

$R^2$ consists of Me, $R^3$ consists of H, and $R^4$ consists of NH2; and wherein for (3), $R^1$ consists of

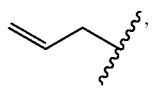 [SMILES: *CC=C]

$R^2$ consists of Me, $R^3$ consists of H, and $R^4$ consists of NH2.

In some embodiments the $R^1$ group may include a terminus or sidechain that includes a lipid and/or fatty acid group and/or an alkane, alkene or alkyne moiety, being saturated or having one or more double or triple bonds. Such groups may be branched or unbranched, substituted or unsubstituted and it may comprise cyclic moieties. Such groups may be present at one or more termini or side locations along the length of the molecule. In certain alternative embodiments the almiramide molecule comprises at least one unsaturated terminus. One or more unsaturated moieties may be present on one or more side chains. The almiramide molecule may be a methyl ester derivative or a carboxylic acid derivative.

Other specific embodiments include the following: A molecule selected from FIG. 7 or a derivative, analogue, sub-component or fragment derived therefrom. A molecule selected from FIG. 7 other than a molecule that occurs in nature. A molecule selected from FIG. 7 other than a molecule that occurs in a cyanobacterium. A molecule from FIG. 7 selected from the group consisting of compounds 13-24 or a derivative, analogue, sub-component or fragment derived therefrom. A molecule selected from FIG. 7 wherein the molecule comprises a N—N-dimethyl-amide C-terminus (13-16) or a derivative, analogue, sub-component or fragment derived therefrom. A molecule selected from FIG. 7 wherein said molecule is a methyl ester derivative (21-24) or a derivative, analogue, sub-component or fragment derived therefrom. A molecule selected from FIG. 7 wherein said molecule is a carboxylic acid derivative (17-20) or a derivative, analogue, sub-component or fragment derived therefrom. A molecule described above having anti-pathogenic properties. A molecule described above having anti-pathogenic properties against *Leishmania* or *Trypanosoma* genus. A molecule described above that binds specifically to a target naturally present in a protozoan parasite. A molecule described above that binds specifically to a target naturally present in *Leishmania* or *Trypanosoma* genus. A method for treating a disease in a subject the method comprising administering to the subject a compound selected from FIG. 7 or a derivative, analogue, sub-component or fragment derived therefrom. A method for treating a disease in a subject the method comprising administering to the subject a compound selected from the group consisting of compounds 13-24 or a derivative, analogue, sub-component or fragment derived therefrom. The method described above wherein the compound does not occur in nature. A method for effecting the physiology of a pathogen, the method comprising contacting the pathogen to a compound selected from FIG. 7 or a derivative, analogue, sub-component or fragment derived therefrom. A method for affecting the physiology of a pathogen, the method comprising contacting the pathogen to a compound selected from the group consisting of compounds 13-24, or a derivative, analogue, sub-component or fragment derived therefrom. The method described above wherein the pathogen is a protozoan. The method above wherein the pathogen is of the genus *Leishmania* or *Trypanosoma*. The method described above wherein compound is selected from the group consisting of compounds 13-24 or a derivative, analogue, sub-component or fragment derived therefrom. The method described above wherein compound selected from FIG. 7 does not occur in the genus *Leishmania*. A method for screening a pool of compounds so as to identify a target compound, the method comprising (i) labelling or immobilizing a first compound selected from FIG. 7 or a derivative, analogue, sub-component or fragment derived therefrom, (ii) providing a pool of second compounds, (iii) contacting first the labelled or immobilized compound with the pool of second compounds under conditions that allow specific binding to occur between the first compound and at least one second compound, (iv) washing the labelled or immobilized first compound so as to remove unbound second compound(s), and (v) purifying and characterising the second compound(s) that have bound specifically to the first compound. The method for screening described above wherein the first compound is selected from the group consisting of compounds 13-24, or a derivative, analogue, sub-component or fragment derived therefrom. The method described above wherein the first compound is immobilized within a chromatography apparatus. The method described above wherein the first compound is labeled with a radioactive, fluorescent, chromatological, color-developing, or immunological marker. A target compound identified by any or the methods described herein. A drug formulation comprising a drug and a carrier, wherein the drug is selected from a compound described in FIG. 7, or a derivative, analogue, sub-component or fragment derived therefrom. The drug formulation described above wherein the drug is selected from the group consisting of compounds 13-24, or a derivative, analogue, sub-component or fragment derived therefrom. A drug formulation comprising a drug and a carrier, wherein the drug comprises a molecule having the structural formula:

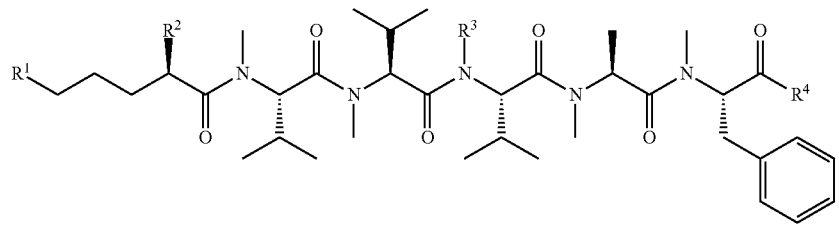

wherein R1, R2, R3, and R4 may be any specie or group. The drug formulation of claim 30 wherein the R1, R2, R3, and R4 are selected from the species disclosed in FIG. 7. The drug formulation described above wherein the drug binds specifically to a compound derived from a protozoan pathogen. The drug formulation of claim 30 wherein the drug binds specifically to a compound derived from a *Leishmania*. The drug formulation described above wherein the drug kills or inhibits the growth, reproduction or otherwise interferes with the life-cycle of a protozoan pathogen. The drug formulation described above wherein the protozoan pathogen is *Leishmania*. A kit for diagnosis of the presence of *Leishmania* in a sample, the kit consisting of a compound selected from the group consisting of compounds 13-24, or a derivative, analogue, sub-component or fragment derived therefrom, wherein, in use, the compound bound to a radioactive, fluorescent, chromatological, color-developing, or immunological marker.

BRIEF DESCRIPTION OF THE FIGURES, SCHEMES AND TABLES

FIG. 1*a*: Almiramides A, B and C
FIG. 1*b*. Subunits a-f and NMR connectivity for 1. Solid arrows=HMBC correlations. Dashed arrows=ROESY correlations.
FIG. 2. Selective semisynthetic methylation of 2 to afford compounds 11 and 12
FIG. 3. Structurally related linear lipopeptides (areas of highest structural homology outlined with dashed lines).
FIG. 4. Generic structure of Almiramide.
FIG. 5. Configurational analysis strategy for 2 and 3
FIG. 6. Formation of semi-synthetic derivatives 11 and 12.
FIG. 7. Structure and Bioactivities of Almiramide A-C and Derivatives.

GENERAL REPRESENTATIONS CONCERNING THE DISCLOSURE

It should be noted that although the present disclosure refers frequently to leishmaniasis and *Leishmania donovani*, the compounds and methods of the invention are directed towards any disease, particularly parasitic diseases caused by amoeba or protozoa or other eukaryotic organisms. Leishmaniasis is given as just one exemplary embodiment. African sleeping sickness and Lyme disease are two other diseases against which the compounds of the invention have a therapeutic effect.

Other diseases against which the compounds and methods of the invention include Amoebiasis, Ascariasis, Babesiosis, Chagas disease, Clonorchiasis, Cryptosporidiosis, Diphyllobothriasis, Dracunculiasis (caused by the Guinea worm), Echinococcosis, Elephantiasis, Enterobiasis, Fascioliasis, Fasciolopsiasis, Filariasis, Giardiasis, Gnathostomiasis, Hymenolepiasis, Isosporiasis, Katayama fever, Lyme disease, Mange, Malaria Metagonimiasis, Myiasis, Onchocerciasis, Pediculosis, Scabies, Schistosomiasis, Strongyloidiasis, Taeniasis (cause of Cysticercosis), Toxocariasis, Toxoplasmosis, Trichinosis, and Trichurias. Other organisms against which the compounds and methods of the invention may be used, either to prevent or treat a disease, include, for example, the following: Anisakis, *Ascaris lumbricoides*, Botfly Balantidium coli, Bedbug, *Cestoda* (tapeworm), Chigger, Hookworm, Liver fluke, Loa loa, Paragonimus (lung fluke), Pinworm, *Plasmodia* (including *falciparum, vivax* and *ovale*), *Schistosoma, Strongyloides stercoralis*, Mites, Tapeworm, *Toxoplasma gondii*, all Trypanosomes, Whipworm, *Wuchereria bancrofti*, and *Ixodes pacificus*.

The term "parasite" in this disclosure is used broadly to mean any organism that is known to cause a pathology by infection of an animal subject (host). Likewise the term "parasitic disease" is used broadly to mean a disease caused by such a parasite. The term "disease" is used to mean any state of an animal that deviates from normal healthy physiology and that is clinically detectable.

The term "binds" or "binding" in connection with the interaction between a compound or molecule and another compound or molecule, such as a target and a potential binding compound, indicates that the potential binding compound associates with the target to a statistically significant degree as compared to association with proteins generally. Thus, the term "specific binding" refers to binding between two molecules or compounds that is statistically significantly higher than non-specific binding to another molecule. Preferably a binding compound interacts with a specified target with a dissociation constant ($k_d$) of 1 mM or less, for example 0.1-100 nM. A binding compound can bind with "low affinity", "very low affinity", "extremely low affinity", "moderate affinity", "moderately high affinity", or "high affinity" as described herein. In the context of compounds binding to a target, the term "greater affinity" indicates that the compound binds more tightly than a reference compound, or than the same compound in a reference condition, i.e., with a lower dissociation constant. In particular embodiments, the greater affinity is at least 2, 3, 4, 5, 8, 10, 50, 100, 200, 400, 500, 1000, or 10,000-fold greater affinity. Also in the context of compounds binding to a biomolecular target, the term "greater specificity" indicates that a compound binds to a specified target to a greater extent than to another biomolecule or biomolecules that may be present under relevant binding conditions, where binding to such other biomolecules produces a different biological activity than binding to the specified target. Typically, the specificity is with reference to a limited set of other biomolecules. In particular embodiments, the greater specificity is at least 2, 3, 4, 5, 8, 10, 50, 100, 200, 400, 500, or 1000-fold greater specificity.

The term "derivative" or "derivative compound" refers to a compound having a chemical structure that contains a common core chemical structure as a parent or reference compound, but differs by having at least one structural difference, e.g., by having one or more substituents added and/or removed and/or substituted, and/or by having one or more atoms substituted with different atoms. Unless clearly indicated to the contrary, the term "derivative" does not mean that the derivative is synthesized using the parent compound as a starting material or as an intermediate, although in some cases, the derivative may be synthesized from the parent.

The term "fragment" refers to a part of a larger whole, for example a fragment of a molecule may be any dissociated part of that molecule, regardless of size.

The term "specie" or "group" when used to describe an "R" group in a chemical formula, is used to mean any chemical compound, sub-compound or substituent that may chemically interact with (covalently, ionically or by Van der Waal's forces) another molecule or group such as shown on a chemical formula.

The terms "formulation", "drug formulation" or "pharmaceutical formulation," refers to a drug combined with a non-drug such as a carrier material designed not to have a pharmaceutical activity, such as pharmaceutical excipient, filler, or carrier material that may be used to modify or improve the drug release, improve its physical and/or chemical stability, dosage form performance, processing, manufacturing, etc.

When a "terminus" or "terminal group" is discussed as having a substituent, side-chain, group or moiety attached, that substituent, side-chain, group or moiety may equally be present at one or more termini or at side locations along the length of the molecule.

The terms "drug" or "therapeutic agent" mean any substance meant to affect the physiology of a subject. Examples of drugs are described in well known literature references such as the Merck Index and the Physicians Desk Reference.

The term "therapeutically effective amount" means an amount of a therapeutic agent, or a rate of delivery of a therapeutic agent, effective to facilitate a desired therapeutic effect. The precise desired therapeutic effect will vary according to the condition to be treated, the formulation to be administered, and a variety of other factors that are appreciated by those of ordinary skill in the art.

The term "diagnostic agent" means any chemical moiety that may be used for diagnosis or in a diagnostic test. For example, diagnostic agents include imaging agents containing radioisotopes, contrasting agents containing for example iodine, enzymes, fluorescent substances and the like.

The term "treatment" means the application of a process to an individual in order to alter a physiological state, whether or not the process includes a curative element.

Where substitutions are mentioned, sometimes in connection with variable "R" groups as shown in the figures, the substituent groups may be selected from, for example, the following: hydrogen, hydroxyl, carboxylate, alkane, alkene or alkyne groups, substituted or unsubstituted heteroatom, alkyl, alkenyl, alkanoyl, aryl, aroyl, aralkyl, alkylamino cycloalkyl, heterocycloalkyl, heteroaryl, or halogen, azido, fluorophore or polypeptide. In certain embodiments the substituent group may comprise branched or un-branched C1-C18 alkyl, C1-C18 substituted alkyl, C1-C18 alkenyl, C1-C18 acyl, amino, substituted amino, wherein the alkyl, alkenyl or acyl is linear or branched, and optionally substituted with a hydroxyl, an ester and its derivatives, 5 a carboxyl and its derivatives. In a particular embodiment, Any R group may be a lower hydrocarbon substituted with alkoxy, substituted alkoxy, imidate, arylthio, or (substituted aryl)thio. In other embodiments, Any R group may be a lower alkyl selected from methyl, ethyl, propyl, isopropyl, butyl, isobutyl, terabutyl and pentyl. In other embodiments, Any R group may be a lower alkenyl selected from vinyl, substituted vinyl, ethynyl, or substituted ethynyl. In other embodiments, Any R group may be a lower alkanoyl selected from formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, and arachidonyl. In other embodiments, Any R group may be lower aryl selected from phenyl, p-tolyl, pchlorophenyl, p-aminophenyl, p-nitrophenyl, p-anisyl. In yet other embodiments, Any R group may be a lower aroyl selected from benzoyl and naphthoyl. In other embodiments, Any R group may be a lower aralkyl selected from benzyl, benzhydryl, p-chlorobenzyl, m-chlorobenzyl, p-nitrobenzyl, benzyloxybenzyl, or pentafluorobenzyl. In certain other embodiments, Any R group may be a lower alkylamino is selected from monoalkylamino, monoaralkylamino, dialkylamino, diaralkylamino, and benzylamino.

It should be noted that the invention encompasses compounds, methods and treatments wherein compounds of the invention, and their derivatives and analogues, sub-components and fragments derived therefrom, may be employed to treat any disease of any organism, either animal or plant.

Although the disclosure refers frequently to leishmaniasis and *Leishmania donovani*, the compounds and methods of the invention are directed towards any disease, particularly parasitic diseases caused by pathogenic eukaryotic organisms such as protozoa. Leishmaniasis is given as just one exemplary embodiment. Other pathogens and diseases are disclosed herein and still further pathogens and diseases may be treated with the compounds of the invention, such as those pathogens and diseases mentioned in the text book "Parasitic Diseases" (5th Edition) by Despommier et al., Apple Trees Productions LLC, Pub., which is hereby incorporated by reference for all purposes.

In this specification, reference is made to particular features of the invention (including for example components, ingredients, elements, devices, apparatus, systems, groups, ranges, method steps, test results, etc). It is to be understood that the disclosure of the invention in this specification includes all appropriate combinations of such particular features. For example, where a particular feature is disclosed in the context of a particular embodiment or a particular claim, that feature can also be used, to the extent appropriate, in the context of other particular embodiments and claims, and in the invention generally. The embodiments disclosed in this specification are exemplary and do not limit the invention. Other embodiments can be utilized and changes can be made. As used in this specification, the singular forms "a", "an", and "the" include plural reference unless the context clearly dictates otherwise. Thus, for example, a reference to "a part" includes a plurality of such parts, and so forth.

The term "comprises" and grammatical equivalents thereof are used in this specification to mean that, in addition to the features specifically identified, other features are optionally present. Where reference is made in this specification to a method comprising two or more defined steps, the defined steps can be carried out in any order or simultaneously. Where reference is made herein to "first" and "second" features, this is generally done for identification purposes; unless the context requires otherwise, the first and second features can be the same or different, and reference to a first feature does not mean that a second feature is necessarily present (though it may be present).

A number of references exist that contain relevant subject matter useful in the understanding of the invention. These include: (1) Linington, R G, J Gonzalez, L-D Urena, L I Romero, E Ortega-Barria, W H Gerwick: Venturamides A and B: Antimalarial Constituents of the Panamanian Marine Cyanobacterium *Oscillatoria* sp. J. Nat. Prod. 70, 397-401 (2007); (2) McPhail, K L, J Correa, R G Linington et al.: Antimalarial Linear Lipopeptides from a Panamanian Strain of the Marine Cyanobacterium *Lyngbya majuscula*. J. Nat. Prod. 70, 984-988 (2007); and (3) Balunas, M. J.; Linington, R. G.; Tidgewell, K.; Fenner, A. M.; Urena, L.-D.; Della Togna, G.; Kyle, D. E.; Gerwick, W. H. "Dragonamide E, a Modified Linear Lipopeptide from *Lyngbya majuscula* with Antileishmanial Activity" J. Nat. Prod., 2010, 73, 60; and (4) Sarath P. Gunasekera et al., "Dragonamides C and D, Linear Lipopeptides from the Marine Cyanobacterium Brown *Lyngbya polychroa*" J. Nat. Prod., 2008, 71 (5), pp 887-890 These references and all documents and publications referred to in this disclosure are hereby incorporated by reference, in their entirety, for all purposes.

The entirely of the "definitions" sections of the following applications are hereby incorporated by reference for all purposes: WO2009114325 and US20060281914.

DETAILED DESCRIPTION OF THE INVENTION

The Panama International Cooperative for Biodiversity Group (ICBG) is investigating Panamanian microorganisms for lead compounds with antileishmanial activity. Initial screening of over 400 pre-fractions from cyanobacterial extracts revealed one fraction from a collection of *Lyngbya majuscula* from Bocas del Toro Marine Park on the Caribbean coast of Panama that exhibited a unique profile against *L. donovani* without showing significant cytotoxicity to mammalian Vero cells. This combination of results indicated the presence of compounds with clinically relevant activity against the target parasite and prompted us to undertake a further investigation of the mixture. Purification of this fraction by $C_{18}$ reversed-phase solid phase extraction chromatography (50% MeOH/$H_2O$ to 100% MeOH) afforded two consecutive active fractions that were further purified by $C_{18}$ RP HPLC to give Almiramides A-C (1-3) as optically active white solids.

Initial NMR analysis of almiramide A (1) in $CD_2Cl_2$ gave spectra that contained two observable conformations in a 3:2 ratio. Reacquisition of these spectra in $CD_3CN$ afforded spectra that also contained two stable conformations, though in a more acceptable ratio of 6:1. Despite the added complexity of interpreting spectra that contain multiple conformers it was possible to identify the presence of subunits a-f (FIG. 1) without significant difficulty. HRESITOFMS gave an [M+H]$^+$ pseudomolecular ion at 743.5062 that was consistent with the molecular formula $C_{40}H_{66}N_6O_7$ (calcd 743.5065), indicating that subunits a-f contained the required number of double bond equivalents and that 1 was a linear lipopeptide. Careful consideration of both HMBC and ROESY data for these subunits as indicated in FIG. 1 allowed for the construction of the planar structure of 1 which was further supported by fragmentation patterns in the mass spectrum.

Almiramide B (2) gave a HRESITOFMS [M+H]$^+$ pseudomolecular ion at 725.4964 that was consistent with the molecular formula $C_{40}H_{64}N_6O_6$ (calcd 725.4960). Cursory examination of the proton spectrum for 2 showed it to possess the same gross structure as 1. A more detailed consideration of the NMR data showed 2 to possess the same peptidic portion as found in 1, implying that the structural variation lay in the lipid sidechain. The absence of the methyl singlet and ketone carbonyl signals from 1 ($\delta_H$ 2.04 $\delta_C$ 29.9 and $\delta_C$ 209.6 respectively) combined with the presence of new quaternary carbon ($\delta_C$ 85.4) and methyne signals ($\delta_H$ 2.16, $\delta_C$ 69.7) for 2 strongly suggested that the terminal ketone of 1 had been replaced with a terminal alkyne in 2. Further consideration of the NMR data for this compound (FIG. 7) confirmed this initial assignment, thus defining the structure of this new metabolite as NH2-Phe-NMe-Ala-NMe-Val-Val-NMe-Val-NMe-COCH($CH_3$)($CH_2$)$_5$C≡CH.

Almiramide C (3) gave a HRESITOFMS [M+H]$^+$ pseudomolecular ion at 727.5115 that was consistent with the molecular formula $C_{40}H_{66}N_6O_6$ (calcd 727.5116). As with almiramide B, consideration of the NMR resonances for the amino acid residues present in 3 showed them to be identical to those for almiramide A (1), suggesting that 3 differed from 1 and 2 in the constitution of the side chain. The presence of three new multiplet proton resonances between $\delta_H$ 4.89 and $\delta_H$ 5.83 and new resonances in the carbon spectrum at $\delta_C$ 115.0 and $\delta_C$ 140.1 coupled with the absence of the quaternary carbon ($\delta_C$ 85.4) and methyne signals ($\delta_H$ 2.16, $\delta_C$ 69.7) for 2 suggested the presence of a mono-substituted olefin in place of the terminal alkyne present in 2. This assignment was confirmed by consideration of the gCOSY, gHSQC and gHMBC spectra for 3 which unequivocally identified the fatty acid terminus as a 2-methyloct-7-enoic acid residue.

Determination of the stereoconfiguration for 1-3 was accomplished using two complimentary approaches (FIG. 5). For the amino acid residues standard Marfey's analysis was employed, and the resulting derivatives analyzed by LC-MS. For the determination of the configuration at the 2 position of the side chain the fatty acid was derivatized with a chiral derivatizing agent and the retention time on GC-MS compared to that of known synthetic standards.

It has been noted that side chains containing a terminal alkyne moiety are not stable to the strongly acidic conditions typically employed in the hydrolysis of peptides. Consequently both 2 and 3 were subjected to hydrogenation over palladium on carbon to form compound 4 prior to hydrolysis in order to preserve the integrity of the side chains. Hydrolysis products were partitioned against 0.1 N HCl and EtOAc to afford the amino acids in the aqueous phase and the side chain in the organic phase. The aqueous portions from all three samples were separately concentrated to dryness in vacuo. The resulting residues were derivatized with $N_\alpha$-(2,4-dinitro-5-fluorophenyl)-L-valinamide (DLVA) under standard conditions and analyzed by gradient $C_{18}$ RP-HPLC in each case. Comparison of the retention times and mass spectra for these derivatives with commercially available standards that had been derivatized with DLVA in an identical fashion unequivocally assigned all amino acid residues as L for almiramides A-C. These assignments were all subsequently confirmed by co-injection analyses.

To determine the configuration of the side chains for 2 and 3 the organic phases from the hydrolysis partitions were separately derivatized with (S)-1-phenylethylamine under standard amide coupling conditions (FIG. 5) to form compound 9. Commercially available (±)-2-methylocatanoic acid was similarly derivatized to give compounds 9 and 10 which were separated by flash silica gel column chromatography. Differentiation of these two products was accomplished by X-ray analysis of compound 9 which defined the structure as (2R)-2-methyl-N-((S)-1-phenylethyl) octanamide. Comparison of the retention times of these synthetic materials by GC analysis with the retention time of the natural product derivatives showed that both 2 and 3 possessed the R configuration at the 2 position of the side chain. This result was somewhat surprising as a recent total synthesis of the related metabolite dragonamide A (5) has shown it to contain the (2S)-2-methyloct-7-ynoic acid moiety. Work from the Panama ICBG has provided evidence that another related metabolite, dragonamide B (6), also contains the (2S)-2-methyloct-7-ynoic acid subunit. 6 was also isolated as a component of an inactive fraction from the crude extract investigated in this study and we therefore analyzed an authentic sample of 6 under identical conditions. GC-MS analysis indicated that (2S)-2-methyl-N-((S)-1-phenylethyl)octanamide (10) was produced as the sole product from the derivatization of 6. This result confirmed the previous configurational assignment and indicated that this organism possesses the biosynthetic capability to produce two closely related compounds (2 and 6) that contain constitutively identical side chains with opposite configurations, likely through a divergent biosynthetic pathway.

By extension of the biosynthetic capability of this organism in the production of the almiramides and comparison of the NMR chemical shifts for 1, 2 and 3 we consider it highly likely that the stereoconfiguration of this center in compound 1 is also R, though this was not verified experimentally.

Biological evaluation of these three compounds showed that compounds 2 and 3 possessed strong in vitro antiparasitic activity against L. donovani (2.38 and 1.91 µM respectively) whereas compound 1 was completely inactive up to 13.5 µM suggesting the requirement of an unsaturated terminus on the side chain for activity. For reference the two most widely used treatments against leishmaniasis (Pentostam® and Miltefosine®) are active in vitro against L. donovani at 44.7 and 0.5 µM respectively. Previous investigations of cyanobacteria from this region by our group have provided a number of related secondary metabolites including carmabin A (7), dragomabin (8) and dragonamides A (5) and B (6). Parallel testing with almiramides A-C showed compounds 5-8 to be inactive up to the highest tested concentrations (10 µg/mL) despite significant structural similarities between these compounds and almiramides B and C (FIG. 3). These data suggest that the active site for 2 and 3 exhibits a high degree of substrate specificity, and show that possession of alkyne and primary amide termini for N-methylated peptides is insufficient for activity against this target organism.

The value of the almiramides as lead molecules for antileishmanial drug development prompted us to further explore the structure activity relationship (SAR) features of these compounds by the generation of semi-synthetic analogues. Hydrogenation of 2 with $H_2$ and 10% palladium on carbon afforded compound 4 in quantitative yield. Biological evaluation showed 4 to be inactive at the highest tested concentration (13.4 µM), supporting the hypothesis that the unsaturated terminus plays an important role in the interaction of these compounds with their biological target. We were next prompted to explore the importance of the primary and secondary amides for activity in 1-3. Methylation of 2 with NaH/MeI afforded a 1:1 mixture of compounds 11 and 12 (FIG. 2) which were active at 1.64 and 2.31 µM respectively. We hypothesize that the improved activity of 11 over 2 is due to the improved bioavailability of 11 due to its increased membrane permeability. There have been a number of studies that recognize the importance of methylation patterns in determining the degree of membrane permeability for both cyclic and linear peptidic small molecules. Given that the addition of the methyl group at Val1-N has little effect on the calculated conformation of 11 versus 2 it is reasonable to suggest that membrane permeability is an important factor in explaining the comparative efficacy of these two closely related compounds. The small quantities of 11 and 12 generated from derivatization of the natural product precluded the use of standard techniques for structure determination. The unequivocal assignment of these structures was however possible by consideration of a combination of $^1$H NMR and MS fragmentation data. $^1$H NMR for 11 showed the absence of the Val1-NH proton doublet at δ 6.58 and the presence of a new methyl singlet at δ 2.94. Coupled with a mass increase of 14 amu in the low resolution electrospray ionisation mass spectrometry (LRESIMS) this strongly suggested that the Val1-NH proton in 2 had been replaced with a methyl group in 11. This was confirmed by consideration of the MS fragmentation pattern which showed characteristic fragments for the loss of sequential amino acid residues starting from the C-terminus. Similarly, $^1$H NMR for 12 showed the absence of both the Val1-NH and the C-terminal-$NH_2$ proton resonances (δ 6.58; δ 5.80 and δ 6.26) and the presence of three additional methyl singlets in the region δ 2.84-2.94 indicating permethylation at these three positions. As with compound 11 this was confirmed by the MS fragmentation pattern in the LRESIMS spectrum. Interestingly the permethyl species displayed a single conformation on the NMR timescale in contrast to compounds 1-3 and 11, all of which exhibit major and minor conformers in their NMR spectra, suggesting that the C-terminal NH protons play an important role in the hydrogen bonding interactions leading to these two conformational states.

Generation of semi-synthetic derivatives with fully methylated peptide backbones and improved pharmacological properties was particularly gratifying as this opened the door to a facile synthetic route for the generation of peptide libraries and the production of large quantities of material for further in vitro and in vivo testing. We therefore elected to undertake the synthesis of a small library of simplified synthetic analogues (13-24) to probe the viability of this scaffold as a lead for future medicinal chemistry drug development. In designing this initial library we were motivated to explore the SAR attributes of both the C- and N-termini in the hope of finding a suitable synthetic analogue from which to launch the construction of larger more complex combinatorial libraries. Fortunately the peptidic nature of these compounds makes them amenable to solid phase peptide synthesis (SPPS) to construct the core frameworks. This approach permits a divergent strategy by which different solid supports can be employed to generate a variety of functional groups at the C-terminus and addition of the unsaturated alkyl chain as the final step on the solid support provides access to structural diversity at the N-terminus. The library was designed in such a way that the closest analogue (13) differed from 12 only in the absence of the methyl group at the α-position of the lipophilic sidechain (Moya-2) while additional library members showed incrementally greater structural divergence.

In brief, the linear pentapeptide precursor was constructed using standard SPPS techniques starting from either Rink amide or chlorotrityl resins. Addition of the appropriate alkyl chain to the pentapeptide by formation of the corresponding amide bond using HBTU and DIPEA was followed by cleavage from the solid support (1% TFA in CH2Cl2 for chlorotrityl resins, 95% TFA 5% TIPS for Rink amide resins). The resulting intermediates were permethylated with NaH/MeI in THF under Argon starting at −78° C. with warming to room temperature, and the reactions were monitored by LC-MS. In all cases, final purification was performed by reversed-phase HPLC (Phenomenex Jupiter C18 column, 4.6×250 mm, 1 mL/min, MeOH/H2O+0.02% HCOOH). Conversion of compounds 17-20 to their corresponding methyl esters (21-24) was accomplished by treatment with TMS-diazomethane in 3:1 C6D6/MeOH.

Gratifyingly, biological evaluation of compounds 13-24 in parallel with the original lead compounds (1-3) identified several compounds with improved potency over the natural products. Specifically, compounds 13-16 containing the N—N-dimethyl-amide C-terminus exhibited strong antileishmanial activities. By contrast the corresponding methyl ester derivatives (21-24) were completely inactive in this screen and the carboxylic acid derivatives (17-20) showed mixed activities.

The synthesis of compounds 13-16 which exhibit improved activity over the initial natural product lead structures is an important finding for two reasons. Firstly this discovery circumvents one of the most common impediments to the development of natural product drug leads by providing an efficient route to a renewable supply of material; an essential requirement for preliminary in vivo studies which typically requires more material than is available from the natural source. Secondly, the peptidic nature of this scaffold makes it an ideal candidate for the construction of targeted combinatorial libraries however the presence of a standard (non-methylated) residue at Val-1 and a chiral center at C-2 of the aglycon makes the large scale synthesis of the natural product a comparatively laborious process. By demonstrating that structural variations are tolerated at these positions we have been able to design an efficient route to a simplified family of synthetic analogues which not only proceeds in high yield but also provides the opportunity for exploring the SAR interdependence of the amino acid residues present in this framework.

For reference, the recent total synthesis of dragonamide A (5) required 17 steps in the longest linear sequence starting from 1,5 pentanediol with an overall yield of 1.92%. By contrast the synthesis of 17 was completed in just 15 steps, all but 2 of which were performed on the solid phase in a total yield of 2.25%.

As an additional benefit, the replacement of the sole secondary amide linkage in the natural products with a tertiary N-methyl-amide removes the possibility of proteolytic degradation in the host system, thus improving the predicted pharmacokinetic properties of this compound class in murine model systems.

Experimental Section

General Experimental Procedures. Optical rotations were measured with a Jasco P1010 polarimeter. UV spectra were acquired on a Shimadzu UV2401-PC spectrophotometer. NMR spectra were acquired on a JEOL Eclipse 400 MHz spectrometer and referenced to residual solvent proton and carbon signals ($\delta_H$ 1.94, $\delta_C$ 1.34 for $CD_3CN$). Low resolution APCI mass spectra were acquired on a JEOL LC-mate mass spectrometer (INDICASAT). Accurate mass ESI mass spectra were acquired on an Agilent ESI-TOF mass spectrometer (Scripps Center from Mass Spectrometry, San Diego). HPLC purifications were performed on an Agilent 1100 series HPLC system employing a G1312A binary gradient pump, a G1322A degasser, a G1314A variable wavelength detector tuned to 210 nm and a Phenomenex Jupiter $C_{18}$ (4.6×250 mm) RP-HPLC column. All solvents were HPLC grade and were used without further purification. X-ray analysis was performed. GC-MS analysis was performed on a Thermo Trace GC equipped with an AI3000 series autosampler and a DSQ EIMS.

Collection. The cyanobacterium Lyngbya majuscula (46.5 g dry wt) was collected by hand from a depth of 0.1-0.3 m from mangrove roots on a small island in the Bocas del Toro National Marine Park, Bocas del Toro Province on the North coast of Panama (09° 16.669' N 82° 09.834' W). The cyanobacterium was strained through a mesh bag to remove excess seawater, frozen on site, and stored at −4° C. until workup. The taxonomy was identified by comparison with characteristics described by Geitler. A voucher was deposited at the Smithsonian Tropical Research Institute, Panama (voucher number PAB-04-NOV-05-7).

Extraction and Isolation. Freshly thawed material was extracted exhaustively with $CH_2Cl_2$/MeOH (2:1, 3×500 mL) and the combined organic extracts partitioned against $H_2O$ (200 mL) and concentrated to dryness in vacuo to give 0.57 g of a dark brown gum. This material was subjected to flash Si gel CC (Aldrich, Si gel 60, 230-400 mesh, 40×180 mm) eluting with: 100% hexanes (300 mL), 9:1 hexanes/EtOAc (300 mL), 8:2 hexanes/EtOAc (300 mL), 6:4 hexanes/EtOAc (300 mL), 4:6 hexanes/EtOAc (300 mL), 2:8 hexanes/EtOAc (300 mL), 100% EtOAc (300 mL), 3:1 EtOAc/MeOH (300 mL), 100% MeOH (300 mL). Two contiguous fractions (100% EtOAc; 3:1 EtOAc/MeOH) showed antileishmanial activity and possessed similar LC-MS and NMR features. These were separately subjected to $C_{18}$ RP-SPE chromatography eluting with: 1:1 $H_2O$/MeOH (30 mL), 4:6 $H_2O$/MeOH (30 mL), 3:7 $H_2O$/MeOH (30 mL), 2:8 $H_2O$/MeOH (30 mL), 1:9 $H_2O$/MeOH (30 mL), 100% MeOH (30 mL), 100% EtOAc (30 mL). The active fractions from these separations were separately subjected to $C_{18}$ RP-HPLC to give from the more polar fraction (Phenomenex Jupiter $C_{18}$ 4.6×250 mm RP-HPLC column, 5 µm, 57% MeOH/43% $H_2O$, 210 nm, 1 mL/min, 24.5 min) almiramide A (1) as a colorless glass (3.5 mg, 0.6% of crude extract, $t_R$=15.4 mins) and almiramide B (2) as a colorless glass (1.9 mg, 0.3% of crude extract, $t_R$=39.1 mins). HPLC of the less polar active fraction (Phenomenex Jupiter $C_{18}$ 4.6×250 mm RP-HPLC column, 5 μm, 62% MeOH/38% $H_2O$, 210 nm, 1 mL/min) gave almiramide B (2) as a colorless glass (3.4 mg, 0.6% of crude extract, $t_R$=16.9 mins) and almiramide C (3) as a colorless glass (1.2 mg, 0.2% of crude extract, $t_R$=40.3 mins).

Almiramide A (1) was obtained as a colorless glass; [a]22D −169.1 (c 0.002, MeOH); UV (MeOH) λmax (log ϵ) 228 (sh) (3.77) nm; IR (film) vmax 2960, 1624 cm-1; for 1H and 13C NMR data, see Table 2; HRESIMS m/z [M+H]+ 743.5062 (calcd for C40H67N6O7, 743.5065)

Almiramide B (2) was obtained as a colorless glass; [a]22D −148.9 (c 0.001, MeOH); UV (MeOH) λmax (log ϵ) 230 (sh) (3.76) nm; IR (film) vmax 2970, 1634 cm-1; for 1H and 13C NMR data, see Table 2; HRESIMS m/z [M+H]+725.4964 (calcd for C40H65N6O6, 725.4960)

Almiramide C (3) was obtained as a colorless glass; [a]22D −136.8 (c 0.001, MeOH); UV (MeOH) λmax (log ϵ) 228 (3.69) nm; IR (film) vmax 2955, 1630 cm-1; for 1H and 13C NMR data, see Table 2; HRESIMS m/z [M+H]+ 727.5115. (calcd for C40H67N6O6, 727.5116)

Hydrogenation of 2 and 3: Authentic samples of 2 and 3 (0.1 mg) were independently dissolved in dry $CH_2Cl_2$ (10 mL). 10% palladium on carbon (2 mg) was added and the suspensions stirred under an atmosphere of $H_2$ (balloon) at room temperature for 16 hours. Each sample was concentrated to dryness under a stream of $N_2$, dissolved in MeOH (1 mL) and filtered through a 13 mm 0.2 μm nylon filter. The resulting filtrates were concentrated to dryness under a stream of $N_2$ and purified by $C_{18}$ RP-HPLC (Phenomenex Jupiter $C_{18}$ 4.6×250 mm RP-HPLC column, 5 μm, 76% MeOH/24% $H_2O$, 210 nm, 1 mL/min) to give pure 4 in each case.

Marfey's Analysis of 1-3: An authentic sample of 1 and hydrogenated samples of 2 and 3 were independently treated with 6N HCl in sealed vials at 120° C. for 18 hr. The solutions were concentrated to dryness in vacuo and treated with a solution of 1-fluoro-2,4-dinitrophenyl-5-L-valine-amide (DLVA) (0.25 mg, 0.8 μmol) in acetone (50 μL) and a solution of 0.1 M $NaHCO_3$ (100 μL) in a sealed vial at 90° C. for 5 min. The reaction mixture was neutralized with 2N HCl (50 μL) and diluted with $CH_3CN$ (100 μL). The resulting solution was analyzed by RP-HPLC employing a Phenomenex Jupiter $C_{18}$ column (4.6×250 mm) and a gradient elution profile of 25% $CH_3CN$/75% $H_2O$ (acidified with 0.05% HCOOH) to 55% $CH_3CN$/45% $H_2O$ (acidified with 0.05% HCOOH) over 60 min at a flow of 0.5 mL/min, monitoring at 340 nm. Retention times in minutes for the derivatized amino acid standards were as follows: L-N-methylalanine 32.2; D-N-methylalanine 32.9; L-valine 35.7; L-N-methylvaline 42.3; L-N-methylphenylalanine 45.7; D-valine and D-N-methylphenylalanine 47.8; D-N-methylvaline 50.3.

Synthesis of 9 and 10: To a stirred solution of (±)-2-methyloctanoic acid (82 mg, 0.52 mmol) in dry $CH_2Cl_2$ (10 mL) at 0° C. was added (S)-1-phenylethylamine (65 μL, 0.57 mmol), $Et_3N$ (57 μL, 0.78 mmol, freshly distilled over $CaH$), 1-Ethyl-3-(3-dimethylaminopropyl)-carbodiimide (109.4 mg, 0.57 mmol) and 4-di(methylamino)pyridine (6 mg, 0.05 mmol). The reaction mixture was allowed to warm to room temperature and stirred for 18 hrs. The volatiles were removed in vacuo and the residue suspended in EtOAc (5 mL) and filtered through Celite. The filtrate was diluted with EtOAc (10 mL) and washed sequentially with 0.2N HCl (25 mL), $H_2O$ (25 mL), 0.1N $NaHCO_3$ (25 mL) and $H_2O$ (25 mL) and concentrated to dryness in vacuo to give a white crystalline solid. This material was purified by two steps of flash silica gel column chromatography (26×250 mm, 100% hexanes to 7:3 hexanes/EtOAc; 14×210 mm, 85:15 hexanes/ EtOAc) to give compounds 9 (33 mg, 24%) and 10 (38.4 mg, 28%) as an optically active crystalline white solid and an optically active colorless glass respectively.

(2R)-2-methyl-N-((S)-1-phenylethyl)octanamide (9): white needles ($^i$PrOH); $[\alpha]^{20}_D$ −85.3 (c 1.3, $CHCl_3$); UV (MeOH); $^1$H NMR ($CDCl_3$, 300 MHz) δ 7.28-7.16 (5H, m), 5.62 (1H, bd, J=7.8 Hz), 5.09 (1H, dq, J=7.3, 7.3 Hz), 2.08 (1H, m), 1.59 (1H, m), 1.43 (3H, d, J=6.9 Hz), 1.33-1.14 (9H, m), 1.05 (3H, d, J=6.8 Hz), 0.82 (3H, t, J=6.7 Hz); $^{13}$C NMR ($CDCl_3$, 75 MHz) δ 175.5, 128.6, 127.3, 126.1, 48.3, 41.7, 34.4, 31.7, 29.3, 27.4, 22.6, 21.7, 17.8, 14.0.

(2S)-2-methyl-N-((S)-1-phenylethyl)octanamide (10): colorless glass; $[\alpha]^{20}_D$ −66.1 (c 1.4, $CHCl_3$); UV (MeOH); $^1$H NMR ($CDCl_3$, 300 MHz) δ; $^{13}$C NMR ($CDCl_3$, 75 MHz) δ 175.6, 128.6, 127.2, 126.1, 48.3, 41.6, 34.4, 31.7, 29.2, 27.4, 22.5, 21.6, 17.8, 14.0.

GC-MS Analysis of 9 and 10: GC-MS analyses were performed on an Altech Chirasil Val column (25 m×0.25 mm, 0.16 μm ID) employing a temperature gradient from 90 to 220° C. at a ramp rate of 4° C./min followed by 5 minutes at 220° C. Retention times in minutes for compounds 9 and 10 were as follows: 9 25.61, 10 25.05.

Methylation of 2: To a stirred solution of 2 (2 mg, 0.002 mmol) in dry THF (1 mL) was added NaH (60% dispersion in oil, 2 mg, 0.05 mmol) and the solution stirred under argon at room temperature for 2 hrs. MeI (50 μL, 0.80 mmol) was added dropwise and the resulting solution stirred for a further 21 hours. The reaction mixture was quenched with water (0.5 mL) and partitioned with EtOAc (2 mL). The phases were separated and the aqueous phase washed with EtOAc (2 mL). The combined organics were concentrated to dryness under a stream of $N_2$ gas and purified by $C_{18}$ RP-HPLC (Phenomenex Jupiter $C_{18}$ 4.6×250 mm RP-HPLC column, 5 μm, 72% MeOH/28% $H_2O$, 210 nm, 0.8 mL/min) to give 11 (0.2 mg, 13%) and 12 (0.6 mg, 38%) as white solids.

Bioassays. All bioassays were performed in duplicate, testing at 10, 2, 0.4, 0.08 and 0.016 μg/mL. Malaria bioassays were performed as previously reported by our program, using chloroquine as a positive control ($IC_{50}$=80-100 nM). Chagas bioassays were performed following the protocol of Buckner et al, and using nifurtimox as a positive control ($IC_{50}$ 3-5 μg/mL). Leishmaniasis bioassays were performed using a method previously employed in our laboratory, based on parasite DNA fluorescence. In this latter assay, amphotericin-B was used as the positive control and had an $IC_{50}$ value of 80 ng/mL. Cytotoxicity bioassays were performed following an MTT cell proliferation assay protocol with green monkey Vero kidney cells.

The invention claimed is:

1. A method for treating a pathogen infection of a host wherein the pathogen is Leishmania donovani, the method comprising exposing the pathogen Leishmania donovani to an almiramide compound, the almiramide compound comprising a linear lipopeptide having the following structure -continued

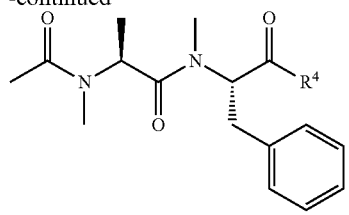

wherein R¹ is selected from one of the following moieties:

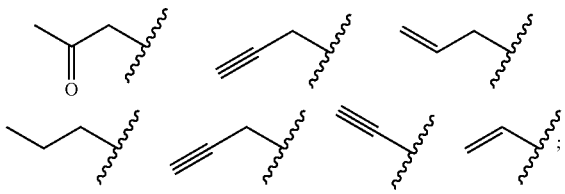

and wherein R² is selected from one of the following moieties: Me or H;
and wherein R³ is selected from one of the following moieties: Me or H;
and wherein R⁴ is selected from one of the following moieties: NH₂, dimethylamindo (NMe₂), hydroxyl (OH), and methoxy (OMe); but specifically excluding compounds (1), (2), and (3)
wherein for (1), R¹ consists of a 2-keto-propyl group ( 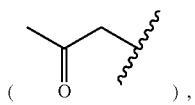 ), R² consists of a methyl group (Me), R³ consists of hydrogen (H), and R⁴ consists of amidogen (NH₂);
and wherein for (2), R¹ consists of a 1-propynyl group ( 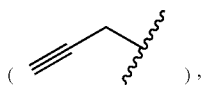 ), R² consists of a methyl group (Me), R³ consists of hydrogen (H), and R⁴ consists of amidogen (NH₂);

and wherein for (3), R¹ consists of a 1-propenyl group ( 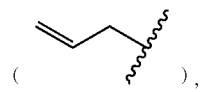 [SMILES: *CC=C] ),

R² consists of a methyl group (Me), R³ consists of hydrogen (H), and R⁴ consists of amidogen (NH₂).

2. The method of claim 1 wherein the almiramide compound is selected from the group consisting of compounds 11, 12, 13, 14, 15, and 16 as shown below:

| Compound | R¹ | R² | R³ | R⁴ |
|---|---|---|---|---|
| 11 | 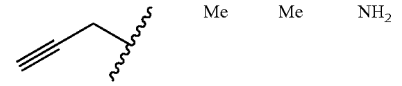 | Me | Me | NH₂ |
| 12 |  | Me | Me | NMe₂ |
| 13 |  | H | Me | NMe₂ |
| 14 | 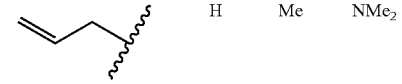 | H | Me | NMe₂ |
| 15 |  | H | Me | NMe₂ |
| 16 | 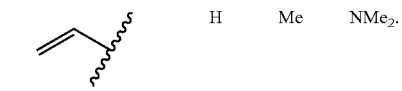 | H | Me | NMe₂. |

3. The method of claim 2 wherein the almiramide compound comprises an N—N-dimethyl-amide C-terminus.

4. The method of claim 2 wherein the almiramide compound is selected from the group consisting of compound 13, compound 14, and compound 16.

* * * * *